US010041871B2

(12) United States Patent
Jamison et al.

(10) Patent No.: US 10,041,871 B2
(45) Date of Patent: Aug. 7, 2018

(54) METHODS AND SYSTEMS FOR TESTING LOST CIRCULATION MATERIALS

(71) Applicant: Halliburton Energy Services, Inc., Houston, TX (US)

(72) Inventors: Dale E. Jamison, Humble, TX (US); Robert J. Murphy, Kingwood, TX (US); Matthew L. Miller, Spring, TX (US); Sharath Savari, Hyderabad (IN)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/883,767

(22) Filed: Oct. 15, 2015

(65) Prior Publication Data

US 2016/0033382 A1 Feb. 4, 2016

Related U.S. Application Data

(62) Division of application No. 13/468,802, filed on May 10, 2012, now Pat. No. 9,188,522.

(51) Int. Cl.
*G01N 11/04* (2006.01)
*G01N 33/28* (2006.01)

(52) U.S. Cl.
CPC ......... *G01N 11/04* (2013.01); *G01N 33/2823* (2013.01)

(58) Field of Classification Search
USPC ..................................... 73/152.18
See application file for complete search history.

(56) References Cited

U.S. PATENT DOCUMENTS

| 4,665,984 A * | 5/1987 | Hayashi .............. E21B 43/26 166/250.1 |
| 5,488,224 A | 1/1996 | Fagan et al. |
| 6,269,684 B1 | 8/2001 | Maki, Jr. et al. |
| 7,900,504 B2 * | 3/2011 | Huynh .................. G01N 15/08 73/38 |
| 2008/0236891 A1 | 10/2008 | Huynh et al. |
| 2010/0139387 A1 | 6/2010 | Jamison et al. |

(Continued)

FOREIGN PATENT DOCUMENTS

| WO | 2008118953 A1 | 2/2008 |
| WO | 2008112795 A1 | 9/2008 |

OTHER PUBLICATIONS

Savari et al, "Improved Lost Circulation Treatment Design and Testing Techniques Minimize Formation Damage", Jun. 2011, SPE143603.

(Continued)

*Primary Examiner* — Paul West
*Assistant Examiner* — Mark A Shabman
(74) *Attorney, Agent, or Firm* — Tenley Krueger; Baker Botts L.L.P.

(57) ABSTRACT

Apparatus and methods for simulation of bore hole fractures are disclosed. A device for simulating a fracture in a subterranean formation comprises a housing, a gap in the housing, and one or more shims positioned inside the gap. The shims cover at least a portion of a surface of a wall forming the gap. The device further comprises an inlet for directing a sample fluid into the gap. The sample fluid flows through the gap and flows out of the gap through an outlet.

22 Claims, 5 Drawing Sheets

(56) References Cited

U.S. PATENT DOCUMENTS

2011/0130965 A1* 6/2011 Slater ............... E21B 21/01
702/9

OTHER PUBLICATIONS

Kumar et al, "Application of Fiber Laden Pill for Controlling Lost Circulation in Natural Fractures", Apr. 2011, AADE-11-NTCE-19.
Office Action issued in related Eurasian Patent Application No. 201491985, dated May 19, 2016 (4 pages).
International Search Report and Written Opinion issued in related International Application No. PCT/US2013/040383, dated Sep. 17, 2013 (10 pages).
International Preliminary Report on Patentability issued in related International Application No. PCT/US2013/040383, dated Nov. 20, 2014 (7 pages).

* cited by examiner

METHODS AND SYSTEMS FOR TESTING LOST CIRCULATION MATERIALS

CROSS-REFERENCE TO RELATED APPLICATION

This application is a divisional of application Ser. No. 13/468,802, filed May 10, 2012, which is incorporated herein by reference in its entirety.

BACKGROUND

The present invention relates to subterranean operations and, more particularly, to apparatus and methods for simulation of bore hole fractures.

Drilling operations play an important role when developing oil, gas or water wells or when mining for minerals and the like. During the drilling operations, a drill bit passes through various layers of earth strata as it descends to a desired depth. Drilling fluids are commonly employed during the drilling operations and perform several important functions including, but not limited to, removing the cuttings from the well to the surface, controlling formation pressures, sealing permeable formations, minimizing formation damage, and cooling and lubricating the drill bit.

When the drill bit passes through porous, fractured or vugular strata such as sand, gravel, shale, limestone and the like, the hydrostatic pressure caused by the vertical column of the drilling fluid exceeds the ability of the surrounding earth formation to support this pressure. Consequently, some drilling fluid is lost to the formation and fails to return to the surface. This loss may be any fraction up to a complete loss of the total circulating drilling fluid volume. This condition is generally known in the art as "Lost Circulation." Failure to control Lost Circulation increases drilling cost and can damage formation production capabilities.

The general practice is to add any number of materials to the drilling fluid which act to reduce or prevent the outward flow of the drilling fluid in a porous and or fractured stratum by sealing pores or cracks, thereby reducing or preventing Lost Circulation. The materials used in this process are commonly referred to as Lost Circulation Materials ("LCM") and may be particles or polymers. Some materials typically used as LCM include, but are not limited to, wood fiber, popped popcorn, straw, bark chips, ground cork, mica, ground and sized minerals and the like.

It is desirable to be able to test the performance of different LCM under controlled condition. Accordingly, it is desirable to provide a device to simulate different characteristics of the subterranean formation of interest and to monitor the performance of LCM under these simulated conditions. Current devices used to simulate performance of LCM include disks with smooth surfaces that form gaps to simulate fractures in the subterranean formations. However, actual fractures encountered during performance of subterranean operations may not have a smooth surface. Specifically, depending on formation characteristics, the gap may be textured. The fracture surface texture may affect the interaction of LCM with the fracture. However, current approaches do not account for this effect.

SUMMARY

The present invention relates to subterranean operations and, more particularly, to apparatus and methods for simulation of bore hole fractures.

In one exemplary embodiment, the present disclosure is directed to a device for simulating a fracture in a subterranean formation comprising: a housing; a gap in the housing; one or more shims positioned inside the gap; wherein the shims cover at least a portion of a surface of a wall forming the gap; an inlet for directing a sample fluid into the gap; wherein the sample fluid flows through the gap; and an outlet for directing the sample fluid out of the gap.

In another embodiment, the present disclosure is directed to a method of analyzing a fluid comprising: directing the fluid through an inlet into a gap having a wall; wherein one or more shims are installed on the wall; analyzing interaction of the fluid with the gap; and flowing the fluid out of the gap through an outlet.

In another embodiment, the present disclosure is directed to a system for analyzing an LCM laden fluid comprising: a housing; a gap formed in the housing comprising a wall; one or more shims detachably coupled to the wall; an inlet for directing a fluid into the gap; wherein a fluid flowing into the gap interacts with the one or more shims; wherein the one or more shims are textured to simulate a fracture in a subterranean formation.

The features and advantages of the present invention will be apparent to those skilled in the art from the description of the preferred embodiments which follows when taken in conjunction with the accompanying drawings. While numerous changes may be made by those skilled in the art, such changes are within the spirit of the invention.

BRIEF DESCRIPTION OF THE DRAWINGS

These drawings illustrate certain aspects of some of the embodiments of the present invention, and should not be used to limit or define the invention.

While embodiments of this disclosure have been depicted and described and are defined by reference to example embodiments of the disclosure, such references do not imply a limitation on the disclosure, and no such limitation is to be inferred. The subject matter disclosed is capable of considerable modification, alteration, and equivalents in form and function, as will occur to those skilled in the pertinent art and having the benefit of this disclosure. The depicted and described embodiments of this disclosure are examples only, and not exhaustive of the scope of the disclosure.

DETAILED DESCRIPTION

Illustrative embodiments of the present invention are described in detail herein. In the interest of clarity, not all features of an actual implementation may be described in this specification. It will of course be appreciated that in the development of any such actual embodiment, numerous implementation-specific decisions may be made to achieve the specific implementation goals, which may vary from one implementation to another. Moreover, it will be appreciated that such a development effort might be complex and time-consuming, but would nevertheless be a routine undertaking for those of ordinary skill in the art having the benefit of the present disclosure.

For purposes of this disclosure, an information handling system may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, an information handling system may be a personal computer, a network storage device, or any other suitable device and may vary in size, shape, performance, functionality, and price. The information handling system may include random access memory ("RAM"), one or more processing resources such as a central processing unit ("CPU") or hardware or software control logic, ROM, and/or other types of nonvolatile memory. Additional components of the information handling system may include one or more disk drives, one or more network ports for communication with external devices as well as various input and output ("I/O") devices, such as a keyboard, a mouse, and a video display. The information handling system may also include one or more buses operable to transmit communications between the various hardware components.

For the purposes of this disclosure, computer-readable media may include any instrumentality or aggregation of instrumentalities that may retain data and/or instructions for a period of time. Computer-readable media may include, for example, without limitation, storage media such as a direct access storage device (e.g., a hard disk drive or floppy disk drive), a sequential access storage device (e.g., a tape disk drive), compact disk, CD-ROM, DVD, RAM, ROM, electrically erasable programmable read-only memory ("EEPROM"), and/or flash memory; as well as communications media such wires, optical fibers, microwaves, radio waves, and other electromagnetic and/or optical carriers; and/or any combination of the foregoing.

The terms "couple" or "couples," as used herein are intended to mean either an indirect or a direct connection. Thus, if a first device couples to a second device, that connection may be through a direct connection, or through an indirect electrical connection via other devices and connections. The term "upstream" as used herein means along a flow path towards the source of the flow, and the term "downstream" as used herein means along a flow path away from the source of the flow. The term "uphole" as used herein means along the drillstring or the hole from the distal end towards the surface, and "downhole" as used herein means along the drillstring or the hole from the surface towards the distal end.

It will be understood that the term "oil well drilling equipment" or "oil well drilling system" is not intended to limit the use of the equipment and processes described with those terms to drilling an oil well. The terms also encompass drilling natural gas wells or hydrocarbon wells in general. Further, such wells can be used for production, monitoring, or injection in relation to the recovery of hydrocarbons or other materials from the subsurface. This could also include geothermal wells intended to provide a source of heat energy instead of hydrocarbons.

The present invention relates to subterranean operations and, more particularly, to apparatus and methods for simulation of bore hole fractures.

Figure 1:
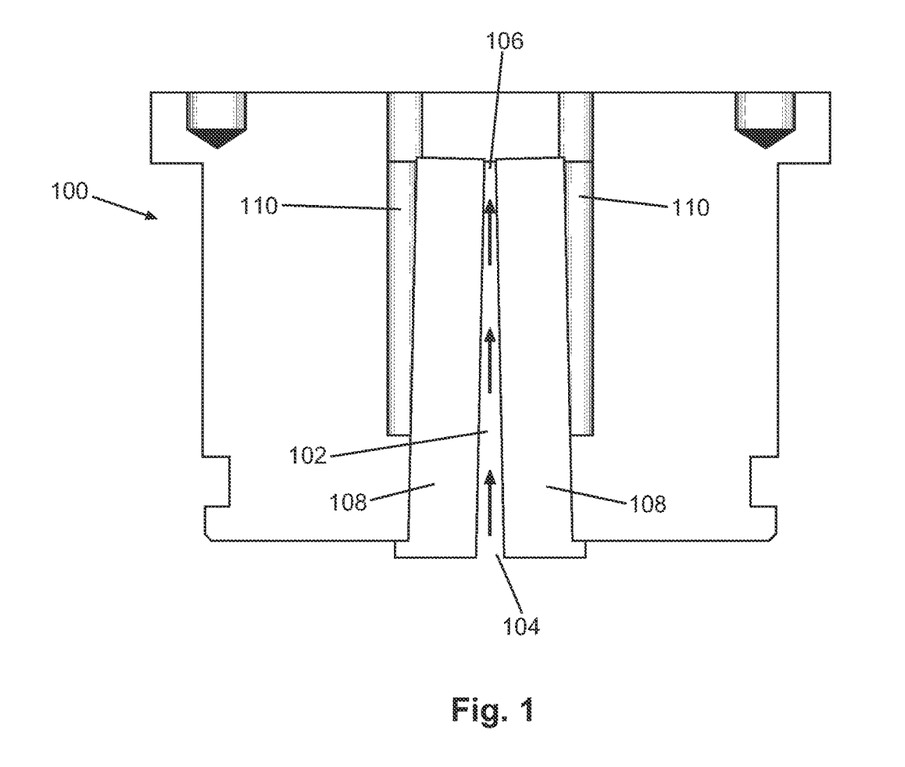
FIG. 1 depicts a Slot Insert (SI) in accordance with an exemplary embodiment of the present invention.
Figure 2:
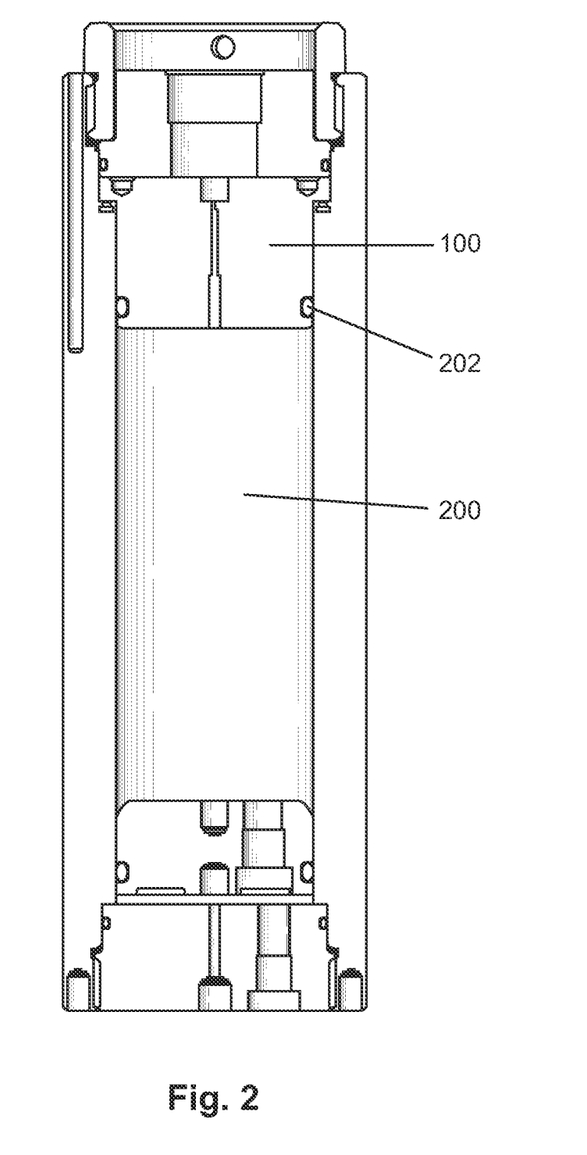
FIG. 2 depicts the SI in accordance with an embodiment of the present disclosure inserted into to a PPA cell.

Turning now to FIG. 1, a Slot Insert ("SI") in accordance with an exemplary embodiment of the present invention is generally denoted with reference numeral 100. The SI 100 may include a housing with a fluid inlet 104 that supplies fluids containing LCM particles to the SI 100 from a source (not shown). In one exemplary embodiment, the source may be a Permeability Plugging Apparatus ("PPA") available from Fann Instrument Company, of Houston, Tex. FIG. 2 depicts the SI 100 in accordance with an embodiment of the present disclosure inserted into a PPA denoted generally with reference numeral 200. In accordance with an embodiment of the present disclosure, one or more O-rings 202 may be used to prevent flow of the LCM laden fluid around the SI 100. The structure and operation of the PPA 200 is well known to those of ordinary skill in the art and will therefore, not be discussed in detail herein.

Returning now to FIG. 1, in one exemplary embodiment, the source may include a pressure or heat generation mechanism that may be used to pressurize and/or heat the sample fluid before it is delivered through the inlet 104. The structure and operation of such heat or pressure generation mechanisms are well known to those of ordinary skill in the art and will therefore not be discussed in detail herein. The flow of the sample fluid from the source through the inlet 104 may be regulated by a valve (not shown). In one exemplary embodiment, the SI 100 may be heated to a regulated test temperature before introducing the sample fluid.

The SI 100 may include a gap 102 to simulate a fracture in a subterranean formation. The gap may be of any size suitable to simulate a fracture and the present disclosure is not limited to a specific gap size. In one example embodiment, the gap may be approximately 1.4 inches long and approximately 1.7 inches wide. In operation, fluid may flow into the gap 102 through the inlet 104 and exit the gap 102 through an outlet 106 as shown by arrows in FIG. 1.

In accordance with an embodiment of the present disclosure, the gap 102 may be set up to simulate the size and/or orientation of a facture in the subterranean formation. For instance, in one embodiment, the gap 102 may be tapered (as shown in FIG. 1). A fluid laden with LCM may then be directed through the gap 102 as shown by arrows in FIG. 1. The operator may then monitor the interaction of the LCM laden fluid with the gap 102 and use that information to predict how effective the LCM laden fluid may be when used during performance of subterranean operations. In accordance with an exemplary embodiment of the present disclosure, the operator may monitor how well the LCM laden fluid fills the gap 102 and/or how much of the LCM laden fluid must be directed through the gap 102 before the gap 102 is effectively plugged. In certain embodiments, the operator may also use the disclosed device and methods to determine how much pressure the plug in the gap 102 can resist.

In accordance with an exemplary embodiment of the present disclosure, one or more shims 108 may be inserted into the gap 102 to line the gap walls. Specifically, the shims 108 are positioned so that at least a portion of the wall forming the gap is covered by the shims 108. The shims 108 may have any thickness deemed best suited for the particular simulation. Accordingly, the present disclosure is not limited to any particular thickness of the shims 108. In one example embodiment, the thickness of the shims 108 may be in a range from approximately 0.125 inches to approximately 0.375 inches.

The shims 108 may be detachably coupled to the walls of the gap 102 in the SI 100. In accordance with an embodiment of the present disclosure, the shims 108 may be made in sets of different thicknesses so that the width of the gap 102 may be varied without changing the angular relationship between the shims 108. In certain embodiments, the SI 100 may include a plurality of different inserts each having a different size gap with the same taper. Moreover, as would be appreciated by those of ordinary skill in the art, with the benefit of this disclosure, multiple size insert pairs may replace the different sized SIs. The shims 108 may have texturing to simulate the texturing of a fracture in the subterranean formation. In accordance with an exemplary embodiment of the present disclosure, the texturing of the shims 108 may be linear with the direction of flow through the gap 102 or it may be perpendicular to the direction of fluid flow through the gap 102. Moreover, the texturing may have a suitable pattern to accurately represent the texturing on the walls of a fracture in the subterranean formation of interest. For instance, the shims 108 may be textured with a circular pattern, a linear pattern, a pattern similar to sand paper, or any other reproducible pattern of controlled roughness.

In accordance with one exemplary embodiment of the present disclosure, the shims 108 may be modified to permit coupling with a porous media. Specifically, a porous media may be coupled to the surface of the shims 108 in the gap 102. This porous media may be made from any suitable materials including, but not limited to, ceramic, sandstone, or sintered metal. In one exemplary embodiment, the backside of the porous media may be fluidically coupled to the downstream side (near the outlet 106) of the gap 102 by a passage 110. This passage 110 may permit fluid flow through the porous media as a plug is formed in the gap 102. In one exemplary embodiment one or more valves (not shown) may be used to control fluid flow through the passage 110.

In accordance with an exemplary embodiment of the present disclosure, the shims 108 may be selected to best represent a particular subterranean formation of interest. Accordingly, the shims 108 may have a textured surface, a smooth surface, or a porous surface. Moreover, in certain embodiments, it may be desirable for the shims 108 to include a mixture of different characteristics to accurately represent a formation of interest. Accordingly, the shims 108 may be mixed to include a textured surface and a porous surface; a smooth surface and a textured surface; or a smooth surface and a porous surface, in the same test.

As would be appreciated by those of ordinary skill in the art, with the benefit of this disclosure, the shims 108 may be held in place inside the gap 102 by any suitable means. Moreover, the shims 108 may be permanently or detachable coupled to the gap 102 walls. In one exemplary embodiment, the shims 108 may be detachably coupled to the walls of the gap 102 by any suitable means, such as, for example, screws. Additionally, in one exemplary embodiment, the shims 108 may be designed so that they are in contact with each other at a distal end, proximate to the narrow portion of a tapered gap 102. This arrangement maintains the shims 108 in place and may prevent movement of the shims 108 in the gap 102 as fluid flows therethrough. In embodiments where the shims 108 are detachably installed inside the gap 102, they may be removed in order to examine the plug of LCM inside the gap 102.

In one exemplary embodiment, the SI 100 may be communicatively coupled to an information handling system (not shown) through a wired or wireless communication system. Use of such communication systems is well known to those of ordinary skill in the art and will therefore not be discussed in detail herein. The information handling system may then be used to monitor fluid flow through the gap 102 and/or control opening and closing of the valves that regulate fluid flow through the gap 102 or the passage 110. Moreover, the information handling system may include computer-readable media to store information regarding performance of different LCM and their interaction with the different types of shims 108 as discussed above.

Figure 3:
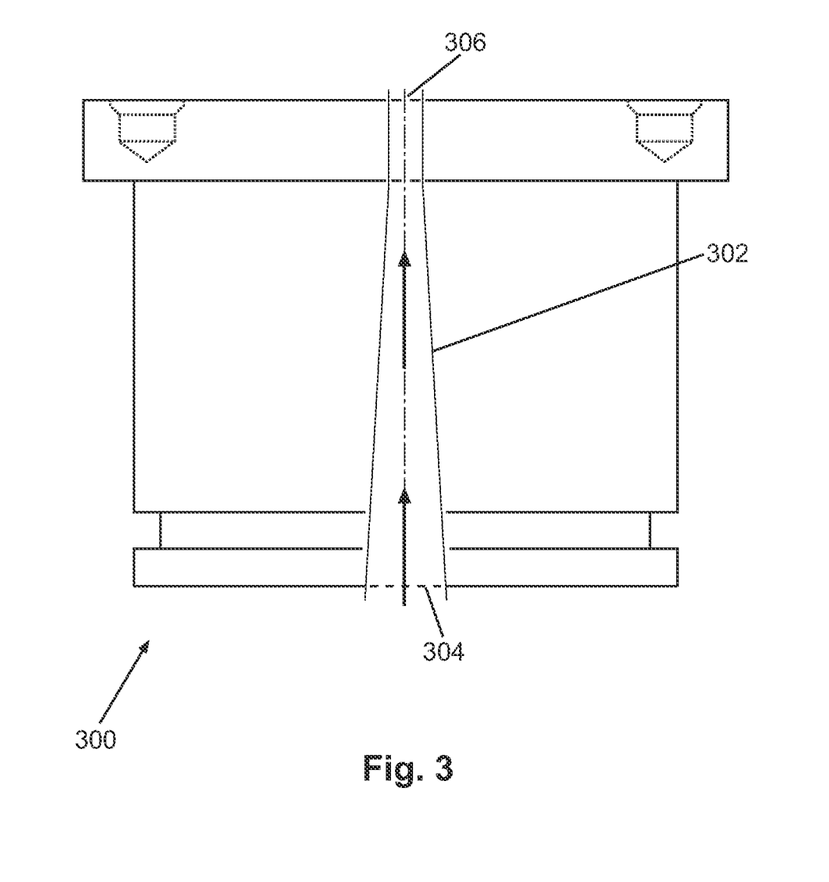
FIG. 3 depicts a Slot Insert (SI) in accordance with another exemplary embodiment of the present invention.

FIG. 3 depicts a Slot Insert ("SI") in accordance with another exemplary embodiment of the present disclosure denoted generally with reference numeral 300. The SI 300 may include a housing with a fluid inlet 304 that supplies fluids containing LCM particles to the SI 300 from a source (not shown). In one exemplary embodiment, the source may be a PPA. The SI 300 may be inserted into the PPA in the same manner as shown in FIG. 2 with respect to the SI 100. The SI 300 may include a gap 302 to simulate a fracture in a subterranean formation. In operation, fluid may flow into the gap 302 through the inlet 304 and exit the gap 302 through an outlet 306 as shown by arrows in FIG. 3.

In accordance with an embodiment of the present disclosure, the gap 302 may be set up to simulate the size and/or orientation of a facture in the subterranean formation. For instance, in one embodiment, the gap 302 may be tapered (as shown in FIG. 3). A fluid laden with LCM may then be directed through the gap 302. The operator may then monitor the interaction of the LCM laden fluid with the gap 302 and use that information to predict how effective the LCM laden fluid may be when used during performance of subterranean operations. In accordance with an exemplary embodiment of the present disclosure, the operator may monitor how well the LCM laden fluid fills the gap 302 and/or how much of the LCM laden fluid must be directed through the gap 302 before the gap 302 is effectively plugged.

In accordance with an embodiment of the present disclosure, the gap 302 may be textured to simulate the texturing of a fracture in the subterranean formation. The texturing of the gap 302 may be linear with the direction of flow through the gap 302 or it may be perpendicular to the direction of fluid flow through the gap 302. Moreover, the texturing may have a suitable pattern to accurately represent the texturing on the walls of a fracture in the subterranean formation of interest. For instance, the gap 302 may be textured with a circular pattern, a linear pattern, a pattern similar to sand paper, or any other reproducible pattern of controlled roughness. Accordingly, the gap 302 may be textured to best represent a particular subterranean formation of interest.

Figure 4:
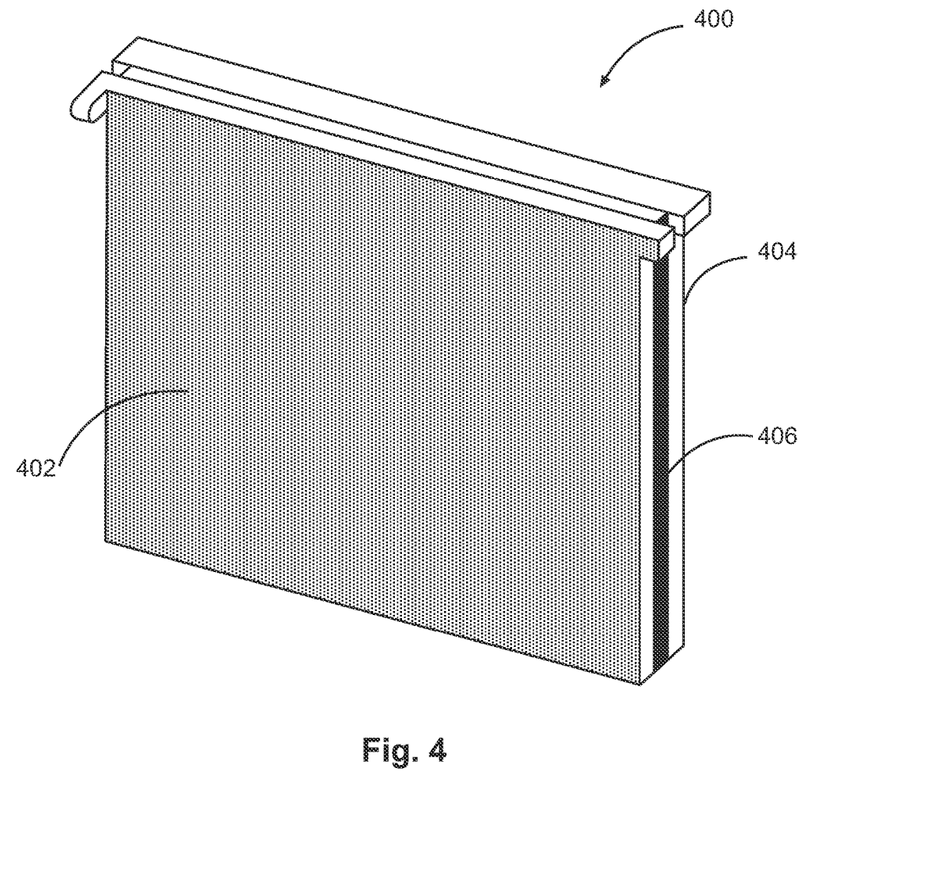
FIG. 4 is a compliant shim in accordance with an exemplary embodiment of the present disclosure.

FIG. 4 shows a compliant shim in accordance with an exemplary embodiment of the present disclosure, denoted generally with reference numeral 400. The compliant shim 400 may be designed so that it may be compressed in the thickness direction with applied pressure to roughly simulate the expansion and contraction of a crack with changing pressure downhole. Specifically, when the pressure is elevated and the LCM laden fluid is forced into the tapered slot as discussed above, the slot would slightly widen while the LCM plug forms to stop the flow. In contrast, when the pressure is subsequently reduced, the slot which simulates the "crack" would try to spring back, putting additional forces on the LCM materials in the slot. If the LCM material is not sufficiently strong, it may be partially pulverized or deformed. Subsequent increases in the pressure may cause the existing plug to fail due to the loss of integrity of the LCM material. LCM materials that are resilient or compress without failure and spring back to their original size may not fail, making them more desirable. Accordingly, the results from a test using compliant shims 400 may provide a valuable comparison of the resulting stress from different LCM materials. In certain embodiments, the compression of the compliant shim 400 may be measured with a displacement sensor to quantify the resulting stress. In one embodiment, the compliant shim 400 may have a metal front piece 402 and a metal back piece 404 with an elastomeric layer 406 therebetween as shown in FIG. 4. In one embodiment, the elastomeric layer 406 may be rubber. As discussed above, the face of the shim (i.e. surface of the front metal piece 402) that is exposed to the fluid may be textured to simulate cracks in a formation. In certain embodiments, the outer surface of the compliant shim 400 may be porous and fluid may be allowed to flow therethrough. Moreover, in certain embodiments, the elastomeric layer 406 may be replaced with springs.

In accordance with certain embodiments, a compliant shim 400 may be subjected to cyclic pressures to help differentiate LCM combinations. Specifically, in drilling operations pumps are turned on and off repeatedly causing pressure variations downhole. Additionally, drill pipe may be moved in and out of the hole also causing pressure variations. These pressure variations may affect LCM materials placed in fractures and pores causing LCM material to dislodge or move and cause fluid leakage and in some cases fracture propagation. Accordingly, cyclic pressures may be used to simulate the normal pressure variations experienced in drilling operations and their impact on a plug formed in the gap 102 of the SI 100. Although application of cyclic pressure is discussed with respect to compliant shim 400, cyclic pressure may also be applied to a SI having a gap with no shims or having a gap with non-compliant shims.

In certain embodiments, the operator may also use the disclosed device and methods to determine how much pressure the plug in the gap 302 can resist. The term "Forward PPA direction" as used herein refers to a configuration where a tapered gap 102 is placed in a PPA with the wider end of the gap 102 located proximate to a bottom portion of the PPA and the narrow end of the gap 102 located proximate to an upper portion of the PPA. Accordingly, fluid flows in through the wider portion of the gap 102 and out through the narrow portion of the gap 102 when it flows in the Forward PPA direction. As would be appreciated by those of ordinary skill in the art, with the benefit of this disclosure, the Forward PPA direction simulates the direction of fluid flow from the wellbore side towards the formation through a fracture in the actual field conditions. The term "Reverse PPA direction" refers to a configuration where the tapered gap 102 is coupled to the PPA in the reverse direction with the narrow end of the gap 102 located proximate to the bottom portion of the PPA 200 and the wider end of the gap 102 located proximate to the upper portion of the PPA. Accordingly, fluid flows in through the narrow portion of the gap 102 and out through the wider portion of the gap 102 when it flows in the Reverse PPA direction. As would be appreciated by those of ordinary skill in the art, with the benefit of this disclosure, the Reverse PPA direction simulates the direction of fluid flow from the formation side towards the wellbore through a fracture in the actual field conditions. This may also be referred to generally as "wellbore breathing". Specifically, when performing subterranean operations, additional dynamic pressures in the wellbore may initiate formation fractures which may take on the drilling fluid. For instance, the circulation of the drilling fluid through the wellbore may create such additional fractures. Consequently, fluids may seep into these additional fractures. Wellbore breathing refers to a condition where once the pumps used in performing subterranean operations are turned off, the fluids that have seeped into these additional fractures leak back into the wellbore. Specifically, once the pumps are turned off and the pressure in the wellbore is reduced and these additional fractures close, the drilling fluid is displaced and causes a surface flow.

Figure 5A:
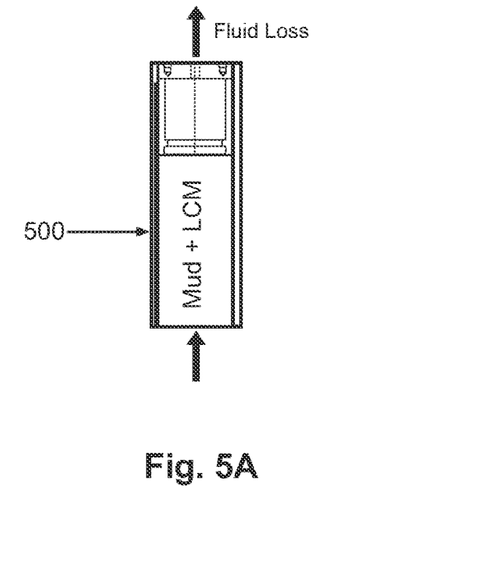
FIGS. 5A and 5B show an arrangement for determining the plug breaking pressure in Forward PPA direction in accordance with an embodiment of the present disclosure.
Figure 5B:
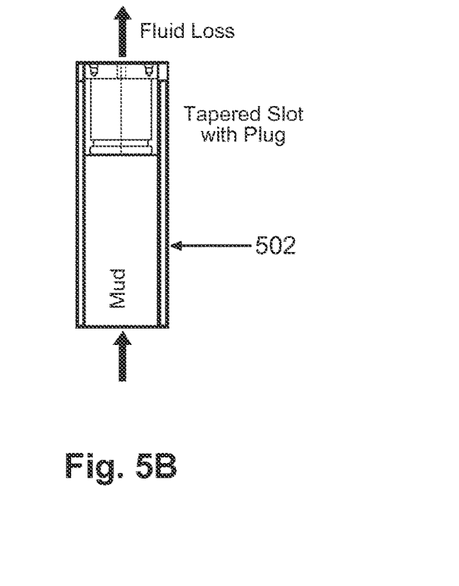

In accordance with an embodiment of the present disclosure, a two step test may be performed to determine how much pressure a plug formed in the gap 102 can resist in each direction. In the first step, as shown in FIGS. 5A and 5B, the plug breaking pressure in Forward PPA direction is determined. A second step, as shown in FIGS. 6A and 6B may entail determining the plug breaking pressure in the Reverse PPA direction.

In the first part of the test, a bridge is formed in the Forward PPA direction. Specifically, a drilling fluid containing LCM particles/fibers may be used to form a plug in the tapered gap 102. The tapered gap 102 is kept within a PPA 500 as shown in FIG. 5A. The arrows in each of FIGS. 5A, 5B, 6A and 6B show the direction of fluid flow through the respective PPA. At a certain differential pressure (e.g. 500 [psi]) the selected LCM forms a plug inside the tapered gap 102 with some amount of fluid loss.

Next, the bridge may be broken in the Forward PPA direction. Specifically, the tapered gap 102 with the LCM plug inside may be placed in another PPA 502 containing a clear drilling fluid (mud) as shown in FIG. 5B. In one embodiment, a hydraulic pump may be used to apply pressure in incremental steps. In one embodiment, the hydraulic pump may apply pressure in incremental steps of 100 [psi]. As the pressure increases, the LCM plug formed in the tapered gap 102 eventually breaks and fluid loss will occur. The pressure at which the LCM plug breaks is determined to be the plug breaking pressure in Forward PPA direction. As would be appreciated by those of ordinary skill in the art, with the benefit of this disclosure, the plug breaking pressure in Forward PPA direction mimics the condition of increased Equivalent Circulating Density ("ECD") or increased pressure in the wellbore that may break the LCM plug and propagate the fracture.

Figure 6A:
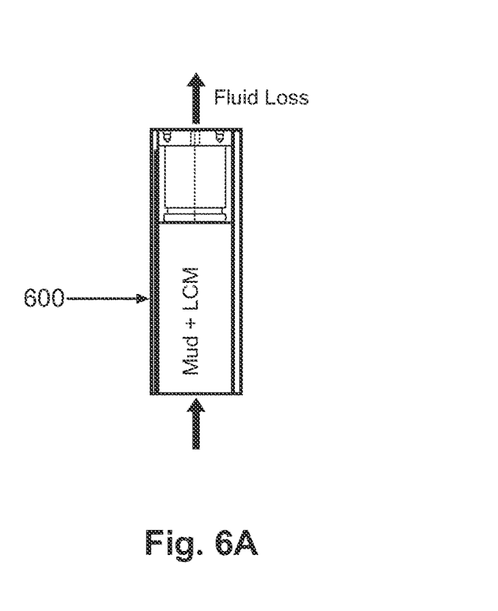
FIGS. 6A and 6B show an arrangement for determining the plug breaking pressure in Reverse PPA direction in accordance with an embodiment of the present disclosure.
Figure 6B:
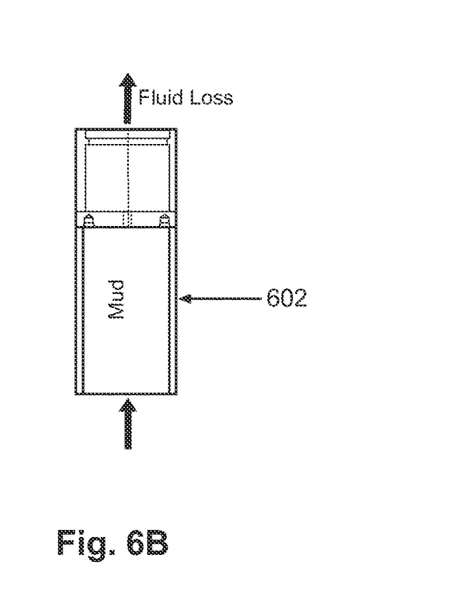

Similar steps as shown in FIG. 6 may be performed to determine the plug breaking pressure in the Reverse PPA direction. Specifically, as shown in FIG. 6A, a drilling fluid containing LCM particles/fibers may be used to form a plug in the tapered gap 102. The tapered gap 102 is kept within a PPA 600 as shown in FIG. 6A. At a certain differential pressure (e.g. 500 [psi]) the selected LCM forms a plug inside the tapered gap 102 with some amount of fluid loss. The tapered gap 102 with the LCM plug is placed inside another PPA 602 containing a clear drilling fluid as shown in FIG. 6B. The tapered gap 102 is placed inside the PPA 602 in the Reverse PPA direction configuration. As would be appreciated by those of ordinary skill in the art, with the benefit of this disclosure, the body of the PPA 602 may need to be slightly modified to permit installation of the SI 100 with the gap 102 oriented to permit flow in the Reverse PPA direction. A hydraulic pump may then be used to apply pressure in incremental steps. In one embodiment, the hydraulic pump may apply pressure in incremental steps of 100 [psi]. As the pressure increases, the LCM plug formed in the tapered gap 102 eventually breaks and fluid loss will occur. The pressure at which the LCM plug breaks is determined to be the plug breaking pressure in Reverse PPA direction. The breaking pressure in Reverse PPA direction may be indicative of the pressure that the LCM plug can withstand when faced with a wellbore breathing condition.

Although the testing to determine how much pressure the plug in the gap 102 can resist is described in conjunction with a tapered gap, the same approach may be used in conjunction with a non-tapered gap. Moreover, the testing procedure disclosed herein is equally applicable to simple tapered slot gaps, tapered slot gaps with shims or tapered slot gaps with compliant shims. In each case, the testing method disclosed herein may be used to determine the pressure the plug in the gap 102 can resist in the Forward PPA direction and/or the Reverse PPA direction.

Therefore, the present invention is well-adapted to carry out the objects and attain the ends and advantages mentioned as well as those which are inherent therein. While the invention has been depicted and described by reference to exemplary embodiments of the invention, such a reference does not imply a limitation on the invention, and no such limitation is to be inferred. The invention is capable of considerable modification, alteration, and equivalents in form and function, as will occur to those ordinarily skilled in the pertinent arts and having the benefit of this disclosure. The depicted and described embodiments of the invention are exemplary only, and are not exhaustive of the scope of the invention. Consequently, the invention is intended to be limited only by the spirit and scope of the appended claims, giving full cognizance to equivalents in all respects. The terms in the claims have their plain, ordinary meaning unless otherwise explicitly and clearly defined by the patentee.

What is claimed is:

1. A method of analyzing a fluid comprising:
   directing the fluid through an inlet into a gap having an immovable wall with a textured surface;
      wherein the fluid interacts with the textured surface as it flows through the gap;
   analyzing interaction of the fluid with the gap;
   forming a plug in the gap;
   applying cyclic pressure to the gap; and
   flowing the fluid through a porous media as the plug is formed in the gap.

2. The method of claim 1, wherein the textured surface simulates a subterranean formation.

3. The method of claim 1, wherein one or more shims are installed on the wall.

4. The method of claim 3, wherein the one or more shims have at least one of a smooth surface, a textured surface, a porous surface, and a combination thereof.

5. The method of claim 1, wherein the gap is a tapered gap.

6. The method of claim 1, wherein analyzing interaction of the fluid with the gap comprises at least one of determining how much fluid flows through the gap before the gap is plugged and determining how much pressure the plug in the gap can resist.

7. The method of claim 6, wherein determining how much pressure the plug in the gap can resist comprises determining how much pressure the plug in the gap can resist in at least one of a Forward PPA direction and a Reverse PPA direction.

8. The method of claim 1, wherein the textured surface comprises a pattern selected from a group consisting of a circular pattern, a linear pattern and a sand paper pattern.

9. The method of claim 1, wherein orientation of texturing of the textured surface is selected from a group consisting of texturing in a direction linear with direction of fluid flow through the gap and texturing in a direction perpendicular with direction of fluid flow through the gap.

10. A system for analyzing fluid flow in a simulated fracture comprising:
    a housing;
    a gap formed in the housing comprising an immovable wall;
    one or more shims detachably coupled to the wall;
    a porous medium coupled to the one or more shims;
    an inlet for directing a fluid into the gap;
       wherein a fluid flowing into the gap interacts with the one or more shims;
       wherein the one or more shims are textured to simulate a fracture in a subterranean formation;
    a pressure device coupled to the gap, wherein the pressure device applies cyclic pressure to the gap; and
    a passage fluidically coupled to the porous medium, wherein the passage permits fluid flow through the porous medium.

11. The system of claim 10, wherein the gap is a tapered gap.

12. The system of claim 11, wherein the one or more shims are arranged to contact each other at a distal end proximate to a narrow end of the gap.

13. The system of claim 10, wherein the one or more shims have at least one of a smooth surface, a textured surface, a porous surface, and a combination thereof.

14. The system of claim 10, wherein the fluid is an LCM laden fluid.

15. A method of analyzing a fluid comprising:
    directing the fluid through an inlet into a gap having an immovable wall, the gap having one or more shims covering at least a portion of the wall;
    wherein the fluid interacts with the one or more shims of the gap as it flows through the gap;
    applying cyclic pressure to the gap;
    analyzing interaction of the fluid with the gap;
    forming a plug in the gap; and
    flowing the fluid through a porous media as the plug is formed in the gap.

16. The method of claim 15, wherein the one or more shims have at least one of a smooth surface, a textured surface, a porous surface, and a combination thereof.

17. The method of claim 16, wherein the textured surface simulates a subterranean formation.

18. The method of claim 16, wherein the textured surface comprises a pattern selected from a group consisting of a circular pattern, a linear pattern and a sand paper pattern.

19. The method of claim 16, wherein orientation of texturing of the textured surface is selected from a group consisting of texturing in a direction linear with direction of fluid flow through the gap and texturing in a direction perpendicular with direction of fluid flow through the gap.

20. The method of claim 15, wherein the gap is a tapered gap.

21. The method of claim 15, wherein analyzing interaction of the fluid with the gap comprises at least one of determining how much fluid flows through the gap before the gap is plugged and determining how much pressure the plug in the gap can resist.

22. The method of claim 21, wherein determining how much pressure the plug in the gap can resist comprises determining how much pressure the plug in the gap can resist in at least one of a Forward PPA direction and a Reverse PPA direction.

* * * * *